(12) United States Patent
Gopalsamy et al.

(10) Patent No.: US 7,250,441 B2
(45) Date of Patent: Jul. 31, 2007

(54) CARBAZOLE AND CYCLOPENTAINDOLE DERIVATIVES TO TREAT INFECTION WITH HEPATITIS C VIRUS

(75) Inventors: Ariamala Gopalsamy, Mahwah, NJ (US); Gregory Mark Ciszewski, Pearl River, NY (US); Mengxiao Shi, New Rochelle, NY (US); Kaapjoo Park, Congers, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/230,729

(22) Filed: Sep. 21, 2005

(65) Prior Publication Data

US 2006/0063821 A1    Mar. 23, 2006

Related U.S. Application Data

(60) Provisional application No. 60/612,144, filed on Sep. 23, 2004.

(51) Int. Cl.
A61K 31/403 (2006.01)
C07D 209/82 (2006.01)

(52) U.S. Cl. ...................... 514/411; 548/448
(58) Field of Classification Search ................ 514/411; 548/448
See application file for complete search history.

(56) References Cited

U.S. PATENT DOCUMENTS 5,830,911 A   11/1998   Failli et al. ................. 514/411

FOREIGN PATENT DOCUMENTS

EP      0 307 077 A    3/1989
WO      WO 98/38986    9/1998
WO      WO 2005/072408 8/2005

OTHER PUBLICATIONS

Davis et al. J. Med. Chem. 1998, 41, 451-467.*
STN search result 7 of 7.*
Gopalsamy, et al. "Identification of carbazole and cyclopentaindole derivatives as inhibitors of HCV RNA dependent RNA polymerase." Abstracts of papers Am. Chem. Soc., vol. 229, part 2, Mar. 2005, p. U167.
Raj, K., et al. "Nu-&Omicron-dialkylaminoalkylcarbaxoles as potential antiviral agents," Indian J. of Chem., Section B: Organic, vol. 14B, No. 5, May 1, 1976, pp. 371-373.

* cited by examiner

*Primary Examiner*—Kamal A. Saeed
*Assistant Examiner*—Yong Chu
(74) *Attorney, Agent, or Firm*—Fitzpatrick, Cella, Harper & Scinto

(57) ABSTRACT

The invention is directed to a method of treating, preventing, or inhibiting a Hepatitis C viral infection in a mammal comprising contacting the mammal with an effective amount of a compound of the formula:

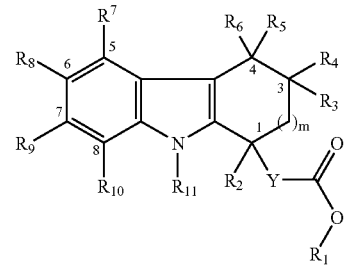

wherein substitutions at $R_1$-$R_{13}$, m and Y are set forth in the specification.

31 Claims, No Drawings

CARBAZOLE AND CYCLOPENTAINDOLE DERIVATIVES TO TREAT INFECTION WITH HEPATITIS C VIRUS

This application claims the benefit of U.S. Provisional Patent Application No. 60/612,144, filed Sep. 23, 2004. That application is hereby incorporated by reference herein in its entirety.

BACKGROUND OF THE INVENTION

1. Field of the Invention

This invention relates to use, preparation, and pharmaceutical compositions of carbazole and cyclopentaindole derivatives, used in the treatment and/or prevention of Hepatitis C viral infection.

2. Related Background Art

Hepatitis C is a common viral infection that can lead to chronic Hepatitis, cirrhosis, liver failure, and hepatocellular carcinoma. Infection with the Hepatitis C virus (HCV) leads to chronic Hepatitis in at least 85% of cases, is the leading reason for liver transplantation, and is responsible for at least 10,000 deaths annually in the United States (Hepatology, 1997, 26 (Suppl. 1), 2S-10S).

The Hepatitis C virus is a member of the Flaviviridae family, and the genome of HCV is a single-stranded linear RNA of positive sense (Hepatology, 1997, 26 (Suppl. 1), 11S-14S). HCV displays extensive genetic heterogeneity; at least 6 genotypes and more than 50 subtypes have been identified.

There is no effective vaccine to prevent HCV infection. The only therapy currently available is treatment with interferon-α (INF-α or combination therapy of INF-α with the nucleoside analog ribavirin (Antiviral Chemistry and Chemotherapy, 1997, 8, 281-301). However, only about 40% of treated patients develop a sustained response, so there is a need for more effective anti-HCV therapeutic agents.

The HCV genome contains a number of non-structural proteins: NS2, NS3, NS4A, NS4B, NS5A, and NS5B (J. General Virology, 2000, 81, 1631-1648). NS5B is an RNA-dependent RNA polymerase which is essential for viral replication, and therefore, the inhibition of NS5B is a suitable target for the development of therapeutic agents.

U.S. Pat. Nos. 5,830,911; 5,776,967; 4,810,699 and 4,782,076 disclose the use of certain compounds of the general formula below (where $R_{11}$=H, Y=$CH_2$ and m=1 or an oxygen atom) as analgesics, anti-inflammatories and as inhibitors of COX-2.

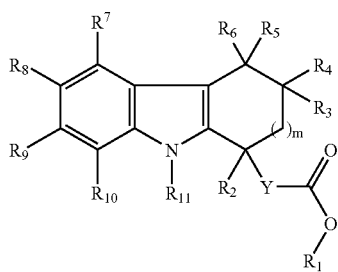

These compounds are also used for treating lymphocytic leukemia in WO 2000002555. Certain compounds (where Y=$CH_2R$, m=1 and $R_{11}$=substituted benzyl) are disclosed as inhibitors of leukotriene synthesis and as prostaglandin antagonists in EP-239306, EP-300676, EP-310179, CA 1299577, EP-468785 and as a medicament for limiting cyclosporin-induced nephrotoxicity in EP307077.

Cyclopentaindole derivatives (where m=0, Y=a bond) are described as useful prostaglandin antagonists in WO200208186. Other compounds (where $R_{11}$=H, m=1, Y=a bond and $R_2$=H) are described as useful antidepressants in DE-2263682 and as useful anti-diabetics in DE-2226702.

None of these prior art references discloses or suggests the use of carbazole and cyclopentaindole derivatives for the treatment and/or prevention of HCV. As noted above, there is a continuing desire for anti-HCV therapeutic agents.

BRIEF SUMMARY OF THE INVENTION

This invention is directed to a pharmaceutical composition useful for the treatment and/or prevention of HCV containing compounds represented by formula (I):

wherein:

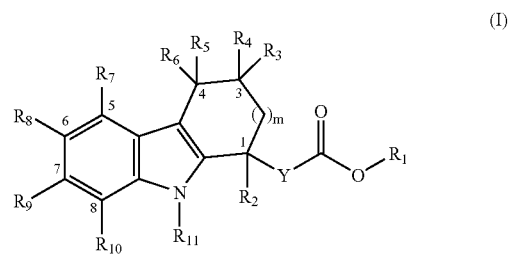

m=0 or 1;

$R_1$ is H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, or an arylalkyl or an alkylaryl of 7 to 12 carbon atoms;

$R_2$ is H, a straight chain alkyl of 1 to 12 carbon atoms, a branched alkyl of 3 to 12 carbon atoms, a cycloalkyl of 3 to 12 carbon atoms, an alkenyl of 2 to 7 carbon atoms, an alkynyl of 2 to 7 carbon atoms, an alkoxyalkyl of 2 to 12 carbon atoms, an arylalkyl or alkylaryl of 7 to 12 carbon atoms, a cyanoalkyl of 1 to 8 carbon atoms, an alkylthioalkyl of 2 to 16 carbon atoms, a cycloalkylalkyl of 4 to 24 carbon atoms, a substituted or unsubstituted aryl, or a substituted or unsubstituted heteroaryl;

$R_3$-$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, a substituted or unsubstituted aryl, furanylmethyl, arylalkyl or alkylaryl of 7 to 12 carbon atoms, alkynyl of 2 to 7 carbon atoms, or $R_5$ and $R_6$ taken together with the ring carbon atom to which they are attached form a carbonyl group;

$R_7$-$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, a substituted or unsubstituted aryl, a substituted or unsubstituted heteroaryl, furanylmethyl, arylalkyl or alkylaryl of 7 to 12 carbon atoms, alkynyl of 2 to 7 carbon atoms, phenylalkynyl, alkoxy of 1 to 8 carbon atoms, arylalkoxy of 7 to 12 carbon atoms, alkylthio of 1 to 8 carbon atoms, trifluoromethoxy, trifluoroethoxy, trifluoromethylthio, trifluo roethylthio, acyl of 1 to 7 carbon atoms, COOH, COO-alkyl, $CONR_{12}R_{13}$, F, Cl, Br, I, CN, $CF_3$, $NO_2$, alkylsulfinyl of 1 to 8 carbon atoms, alkylsulfonyl of 1 to 6 carbon atoms, pyrrolidinyl, or thiazolidinyl;

$R_{11}$ is H, straight chain alkyl of 1 to 6 carbon atoms, branched alkyl of 3 to 10 carbon atoms, cycloalkyl of 3 to 10 carbon atoms, alkenyl of 2 to 7 carbon atoms, or arylalkyl of 7 to 12 carbon atoms;

$R_{12}$-$R_{13}$ are independently H, straight chain alkyl of 1 to 8 carbon atoms, branched alkyl of 3 to 12 carbon atoms, cycloalkyl of 3 to 12 carbon atoms, a substituted or unsubstituted aryl or heteroaryl; and Y is a bond, $CH_2$, $CH_2CH_2$, aryl, or $R_2$ and Y together with the ring carbon atom to which they are attached may additionally form a spirocyclic cycloalkyl ring of 3 to 8 carbon atoms; or a crystalline form or a pharmaceutically acceptable salt thereof; and a pharmaceutically acceptable carrier.

For purposes of this invention the term "alkyl" includes both straight and branched alkyl moieties, preferably of 1 to 8 carbon atoms. The term "alkenyl" refers to a radical aliphatic hydrocarbon containing one double bond and includes both straight and branched alkenyl moieties of 2 to 7 carbon atoms. Such alkenyl moieties may exist in the E or Z configurations; the compounds of this invention include both configurations. The term "alkynyl" includes both straight chain and branched moieties containing 2 to 7 carbon atoms having at least one triple bond. The term "cycloalkyl" refers to alicyclic hydrocarbon groups having 3 to 12 carbon atoms and includes but is not limited to: cyclopropyl, cyclobutyl, cyclopentyl, cyclohexyl, cycloheptyl, norbornyl, or adamantyl. For purposes of this invention the term "aryl" is defined as an aromatic hydrocarbon moiety and may be substituted or unsubstituted. An aryl may be selected from but not limited to, the group: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups. In one embodiment the substituted aryl may be optionally mono-, di-, tri- or tetra-substituted with substituents selected from, but not limited to, the group consisting of alkyl, acyl, alkoxycarbonyl, alkoxy, alkoxyalkyl, alkoxyalkoxy, cyano, halogen, hydroxy, nitro, trifluoromethyl, trifluoromethoxy, trifluoropropyl, amino, alkylamino, dialkylamino, dialkylaminoalkyl, hydroxyalkyl, alkoxyalkyl, alkylthio, —$SO_3H$, —$SO_2NH_2$, —$SO_2NHalkyl$, —$SO_2N(alkyl)_2$, —$CO_2H$, $CO_2NH_2$, $CO_2NHalkyl$, and —$CO_2N(alkyl)_2$. Preferred substituents for aryl and heteroaryl include: alkyl, halogen, amino, alkylamino, dialkylamino, trifluoromethyl, trifluoromethoxy, arylalkyl, and alkylaryl.

For purposes of this invention the term "heteroaryl" is defined as an aromatic heterocyclic ring system (monocyclic or bicyclic) where the heteroaryl moieties are five or six membered rings containing 1 to 4 heteroatoms selected from the group consisting of S, N, and O, and include but is not limited to: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, pyrrolidinyl; (2) a bicyclic aromatic heterocycle where a phenyl, pyridine, pyrimidine or pyridizine ring is: (i) fused to a 6-membered aromatic (unsaturated) heterocyclic ring having one nitrogen atom; (ii) fused to a 5 or 6-membered aromatic (unsaturated) heterocyclic ring having two nitrogen atoms; (iii) fused to a 5-membered aromatic (unsaturated) heterocyclic ring having one nitrogen atom together with either one oxygen or one sulfur atom; or (iv) fused to a 5-membered aromatic (unsaturated) heterocyclic ring having one heteroatom selected from O, N or S.

For the purposes of this invention the term "alkoxy" is defined as (C1-C12)alkyl-O—; the term "aryloxy" is defined as aryl-O—; the term "heteroaryloxy" is defined as heteroaryl-O—; wherein alkyl, aryl, and heteroaryl are as defined above.

For purposes of this invention the term "arylalkyl" is defined as aryl-(C1-C6)-alkyl-; arylalkyl moieties include benzyl, 1-phenylethyl, 2-phenylethyl, 3-phenylpropyl, 2-phenylpropyl and the like.

For purposes of this invention the term "alkylaryl" is defined as (C1-C6)-alkyl-aryl-.

For purposes of this invention the term "alkylthio" is defined as (C1-C6)-alkyl-S—.

For purposes of this invention "alkoxyalkyl," "cycloalkylalkyl," "alkylthioalkyl," "aryloxyalkyl," and "heteroaryloxyalkyl" denote an alkyl group as defined above that is further substituted with an alkoxy, cycloalkyl, alkylthio, aryloxy, or heteroaryloxy group as defined above.

For purposes of this invention "arylalkoxy," "alkoxyalkoxy," "alkylthioalkoxy," and "heteroarylalkoxy" denote an alkoxy group as defined above that is further substituted with an aryl, alkoxy, alkylthio, or heteroaryl group as defined above.

For purposes of this invention "arylthio" and "heteroarylthio," denote a thio group that is further substituted with an aryl or heteroaryl group as defined above.

For purposes of this invention "arylthioakyl" and "heteroarylthioalkyl" denote an alkyl group as defined above that is further substituted with an arylthio or heteroarylthio group as defined above.

For purposes of this invention the term "arylalkylthio" is defined as aryl-(C1-C8)-alkyl-S—; "heteroarylalkylthio" is defined as heteroaryl-(C1-C8)-alkyl-S—, where aryl and heteroaryl are as defined above.

For purposes of this invention "aryloxyalkylthio" is defined as aryloxy-(C1-C8)-alkyl-S; "heteroaryloxyalkylthio" is defined as heteroaryloxy-(C1-C8)-alkyl-S—; where aryloxy, heteroaryloxy, and alkyl are defined above.

For purposes of this invention "phenylalkynyl" is an alkynyl group further substituted with a phenyl group.

In the most preferred embodiment of this invention a substituted methyl comprises a methyl substituent further substituted with for example a furanyl group. In another embodiment of this invention a furanyl substituent is further substituted with a methyl group.

In one preferred embodiment of this invention trifluoromethoxy is $CF_3O$—. In another embodiment of this invention trifluoromethylthio is $CF_3S$—.

In one embodiment of this invention trifluoroethoxy includes but is not limited to $CF_3CH_2O$—. In another embodiment of this invention trifluoroethylthio includes but is not limited to $CF_3CH_2S$—.

The terms "monoalkylamino" and "dialkylamino" refer to moieties with one or two alkyl groups wherein the alkyl chain is 1 to 8 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1 to 8 carbon atoms.

"Acyl" is a radical of the formula —(C=O)-alkyl or —(C=O)-perfluoroalkyl wherein the alkyl radical or perfluoroalkyl radical is 1 to 7 carbon atoms; preferred examples include but are not limited to, acetyl, propionyl, butyryl, trifluoroacetyl.

For purposes of this invention the term "alkylsulfinyl" is defined as a R'SO-radical, where R' is an alkyl radical of 1 to 8 carbon atoms. Alkylsulfonyl is a R'SO$_2$— radical, where R' is an alkyl radical of 1 to 8 carbon atoms. Alkylsulfonamido, alkenylsulfonamido, alkynylsulfonamido are R'SO$_2$NH— radicals, where R' is an alkyl radical of 1 to 8 carbon atoms, an alkenyl radical of 2 to 8 carbon atoms, or an alkynyl radical of 2 to 8 carbon atoms, respectively.

Saturated or partially saturated heteroaryl groups are defined in this invention as heterocyclic rings selected from but not limited to the moieties: azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

For purposes of this invention, the term "BB7" denotes an RNA-dependent RNA polymerase hepatitis C virus protein sequence which is derived from HCV replicon. A discussion of BB7 and related technology can be found in Blight, K. et al. (2000) Science 290:1972-1974. BB7 can be licensed from Apath, LLC (893 North Warson Road, Saint Louis, Mo. 63141, USA). BB7 is also referred to as Con1 HCV sequence and discussions of Con1 can be found in the following references: Lohmann, V. et al. (1999) Science 285:110-113; Pietschmann, T. et al. (2001) J. Virol. 73:1252-1264; and Lohmann, V. et al. (2001) J. Virol. 75:1437-1449.

The compounds used in this invention may contain an asymmetric carbon atom and some of the compounds of this invention may contain one or more asymmetric centers and may thus give rise to stereoisomers, such as enantiomers and diastereomers. The stereoisomers of the instant invention are named according to the Cahn-Ingold-Prelog System. While shown without respect to stereochemistry in Formula (I), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center.

For compounds used in this invention containing two chiral centers, four possible stereoisomers are possible; these four stereoisomers are classified as two racemic pairs of diastereomers. These compounds used in this invention may be present as racemic diastereomers which would be designated following the convention described in the 1997 Chemical Abstracts Index Guide, Appendix IV (Columbus, Ohio) whereas the first cited chiral atom is designated R* and the next cited chiral atom is designated R* if it possesses the same chirality as the first cited stereocenter or S* if it possesses opposite chirality to the first cited stereocenter.

Alternatively, these compounds of the invention may be present as non-racemic mixtures of two diastereomers owing to the existence of a predefined stereocenter. In these instances, the predefined stereocenter is assigned based on the Cahn-Ingold-Prelog System and the undefined stereocenter is designated R* to denote a mixture of both R and S stereoisomers at this center. Compounds used in this invention which possess two chiral centers but which are present as single stereoisomers are described using the Cahn-Ingold-Prelog System.

Pharmaceutically acceptable salts of the compounds of formula (I) having acidic moieties at $R_3$, $R_4$, $R_5$, $R_6$, $R_7$, $R_8$, $R_9$, or $R_{10}$ may be formed from organic and inorganic bases. For example alkali metal salts: sodium, lithium, or potassium and N-tetraalkylammonium salts such as N-tetrabutylammonium salts. Similarly, when a compound of this invention contains a basic moiety at $R_3$, $R_4$, $R_5$, $R_6$, $R_7$, $R_8$, $R_9$, or $R_{10}$, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids.

In one embodiment, the present invention provides for a method of inhibiting the Hepatitis C RNA-dependent RNA polymerase NS5B. The method comprises contacting a cell with an amount of a compound of formula I effective to decrease or prevent NS5B function. The cell may be a mammalian cell and more specifically a human cell. The cell may also be a bacterial cell such as for example E coli. The cell may include but is not limited to, a neuronal cell, an endothelial cell, a glial cell, a microglial cell, a smooth muscle cell, a somatic cell, a bone marrow cell, a liver cell, an intestinal cell, a germ cell, a myocyte, a mononuclear phagocyte, an endothelial cell, a tumor cell, a lymphocyte cell, a mesangial cell, a retinal epithelial cell, a retinal vascular cell, a ganglion cell or a stem cell. The cell may be a normal cell, an activated cell, a neoplastic cell, a diseased cell, or an infected cell.

In another embodiment, the present invention provides a method for the treatment or prevention of Hepatitis C infection in a mammal. The present invention accordingly provides to a mammal, a pharmaceutical composition that comprises a compound of formula I in combination or association with a pharmaceutically acceptable carrier. The compound used in this invention may be administered alone or in combination with other therapeutically effective compounds or therapies for the treatment or prevention of Hepatitis C viral infection in a mammal.

The pharmaceutical compositions are preferably provided orally or subcutaneously. The compositions may be provided by intralesional, intraperitoneal, intramuscular or intravenous injection; infusion; liposome-mediated delivery; topical, nasal, anal, vaginal, sublingual, urethral, transdermal, intrathecal, ocular or otic delivery. In order to obtain consistency in providing the composition of this invention it is preferred that the composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds used in the present invention can be administered orally at a dose range of about 0.01 to 100 mg/kg or preferably at a dose range of 0.1 to 10 mg/kg. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The composition of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, the compounds used in the invention would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds used in the present invention may be delivered together with suitable diluents, preservatives, solubilizers, emulsifiers, adjuvants and/or carriers useful in treatment or prevention of Hepatitis C viral infection. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), antioxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the compound capable of treating or preventing a Hepatitis C viral infection.

The compounds used in the present invention may be delivered locally via a capsule that allows a sustained release of the compound over a period of time. Controlled or sustained release compositions include formulation in lipophilic depots (for example, fatty acids, waxes, oils).

The present invention further provides compounds of formula (I) for use as an active therapeutic substance for preventing Hepatitis C infection. Compounds of formula (I) are of particular use for the treatment of infection with Hepatitis C virus.

The present invention further provides a method of treating Hepatitis C infection in humans, which comprises administering to the infected individual an effective amount of a compound of formula (I) or a pharmaceutical composition of the invention.

The following experimental details are set forth to aid in an understanding of the invention, and are not intended, and should not be construed, to limit in any way the invention set forth in the claims that follow thereafter.

DETAILED DESCRIPTION OF THE INVENTION

The compounds used in the present invention can be readily prepared according to the following reaction schemes or modification thereof. In the following reaction schemes $R_1$, $R_2$, $R_3$, $R_4$, $R_5$, $R_6$, $R_7$, $R_8$, $R_9$, $R_{10}$, $R_{11}$, $R_{12}$, $R_{13}$, m and Y are selected from the groups defined above.

Preferred compounds used in the present invention can be synthesized as described in the schemes below (Scheme 1-2). Cyclohexanecarboxylate (1) is alkylated with an appropriate alkyl halide using sodium hydride in toluene. This is then treated with hydrazine (3) in a sodium acetate/methanol solution to obtain the hydrazone addition product (4). The hydrazone is treated with $BF_3$-EtO to get the cyclopentaindole (5). Deesterification using LiOH/EtOH affords the carboxylic acid product (6).

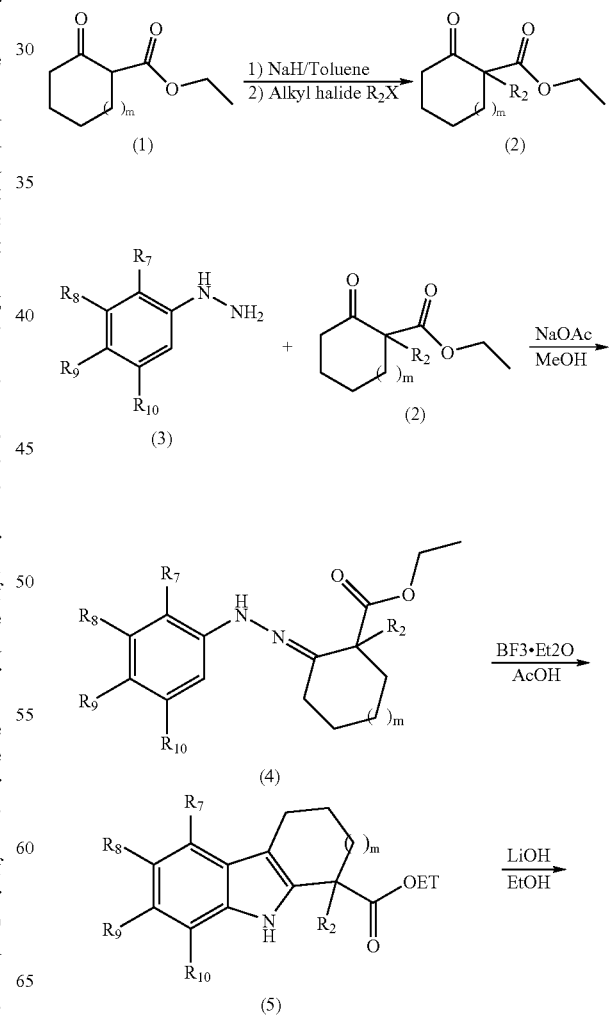

Scheme 1

-continued

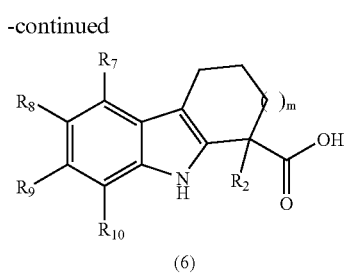

(6)

Scheme 2 shows the addition of a cyano group by treating a compound where $R_7$ is Br with CuCN prior to deesterification using LiOH.

Scheme 2

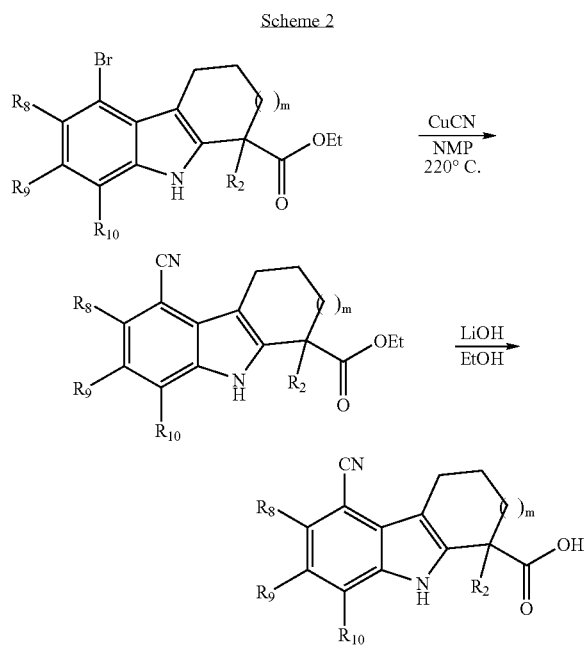

The following non-limiting specific examples are included to illustrate the synthetic procedures used for preparing compounds of the formula (I). In these examples, all chemicals and intermediates are either commercially available or can be prepared by standard procedures found in the literature or are known to those skilled in the art of organic synthesis.

EXAMPLE 1

3-Allyl-5,8-dichloro-1,2,3,4-tetrahydro-cyclopenta[b]indole-3-carboxylic acid

Step 1: 2-carbethoxy-2-allylcyclopentanone

Sodium hydride (1.3 g, 33 mmol) was suspended in anhydrous toluene (15 mL) and the suspension was cooled to 0° C. under nitrogen atmosphere. A solution of 2-carbethoxy-cyclopentaone (4.7 g, 30 mmol) in anhydrous toluene (15 mL) was added dropwise over 20 minutes. The reaction mixture was allowed to warm to room temperature and stirred for another 15 minutes. Allyl bromide (3.0 mL, 33 mmol) was added and the reaction mixture was refluxed over night. The reaction was cooled to room temperature and quenched by adding 50 mL of water. The reaction mixture was extracted with 50 mL of ethyl acetate three times. The combined organic layers were washed with 50 mL of brine and dried over sodium sulfate and concentrated. The residue was purified by flash chromatography (silica gel 60, eluted with 10% ethyl acetate/hexane) to give 2-carbethoxy-2-allylcyclopentanone (3.6 g, 61% yield).

Step 2: 1-Allyl-2-[(2,5-dichloro-phenyl)-hydrazono]-cyclopentanecarboxylic acid ethyl ester To a solution of 2-carbethoxy-2-allylcyclopentanone (110 mg, 0.55 mmol) in 1 mL of methanol was added (2,5-dichloro-phenyl)-hydrazine (89 mg, 0.50 mmol) and sodium acetate (62 mg, 0.75 mmol). The reaction mixture was stirred at room temperature over night. The reaction mixture was concentrated and adding 10 mL of ethyl acetate diluted the residue. The organic solution was washed with 5 mL of water and 5 mL of brine. The organic layer was dried over sodium sulfate and concentrated to give the crude product, which was directly used in next step without purification.

Step 3: 3-Allyl-5,8-dichloro-1,2,3,4-tetrahydro-cyclopenta[b]indole-3-carboxylic acid ethyl ester To the solution of 1-Allyl-2-[(2,5-dichloro-phenyl)-hydrazono]cyclopentane-carboxylic acid ethyl ester (0.50 mmol) in 1.5 mL of acetic acid was slowly added boron trifluoride etherate (80 mg, 0.55 mmol). The reaction mixture was stirred at 114° C. for 2 hours and cooled to room temperature. The reaction mixture was partitioned between ethyl acetate (5 mL) and water (5 mL). The organic layer was washed with saturated sodium bicarbonate aqueous solution (5 mL) and brine (5 mL). The organic solution was collected and concentrated to give crude product.

Step 4: 3-Allyl-5,8-dichloro-1,2,3,4-tetrahydro-cyclopenta[b]indole-3-carboxylic acid To 3-Allyl-5,8-dichloro-1,2,3,4-tetrahydro-cyclopenta[b]indole-3-carboxylic acid ethyl ester was added 1 mL of 2.0 M lithium hydroxide aqueous solution and 1 mL of ethanol. The reaction mixture was stirred at room temperature for 2 hours than concentrated. The residue was purified by reverse phase HPLC to give the desired product.

EXAMPLE 2

3-Butyl-5,8-dichloro-1,2,3,4-tetrahydro-cyclopenta[b]indole-3-carboxylic acid

The title compound was prepared in a manner similar to that of Example 1.

EXAMPLE 3

5,8-Dichloro-3-propyl-1,2,3,4-tetrahydro-cyclopenta[b]indole-3-carboxylic acid

The title compound was prepared in a manner similar to that of Example 1.

EXAMPLE 4

8-Bromo-3-butyl-5-methyl-1,2,3,4-tetrahydro-cyclopenta[b]indole-3-carboxylic acid The title compound was prepared in a manner similar to that of Example 1.

EXAMPLE 5

8-Bromo-3-butyl-5-fluoro-1,2,3,4-tetrahydro-cyclopenta[b]indole-3-carboxylic acid The title compound was prepared in a manner similar to that of Example 1.

EXAMPLE 6

8-Bromo-3-butyl-7-fluoro-5-methyl-1,2,3,4-tetrahydro-cyclopenta[b]indole-3-carboxylic acid The title compound was prepared in a manner similar to that of Example 1.

EXAMPLE 7

3-Butyl-7-fluoro-5-methyl-1,2,3,4-tetrahydro-cyclopenta[b]indole-3-carboxylic acid The title compound was prepared in a manner similar to that of Example 1.

EXAMPLE 8

3-Allyl-8-bromo-5-methyl-1,2,3,4-tetrahydro-cyclopenta[b]indole-3-carboxylic acid The title compound was prepared in a manner similar to that of Example 1.

EXAMPLE 9

3-Allyl-8-bromo-5-fluoro-1,2,3,4-tetrahydro-cyclopenta[b]indole-3-carboxylic acid The title compound was prepared in a manner similar to that of Example 1.

EXAMPLE 10

3-Allyl-8-bromo-7-fluoro-5-methyl-1,2,3,4-tetrahydro-cyclopenta[b]indole-3-carboxylic acid The title compound was prepared in a manner similar to that of Example 1.

EXAMPLE 11

8-Bromo-5-methyl-3-propyl-1,2,3,4-tetrahydro-cyclopenta[b]indole-3-carboxylic acid The title compound was prepared in a manner similar to that of Example 1.

EXAMPLE 12

8-Bromo-5-fluoro-3-propyl-1,2,3,4-tetrahydro-cyclopenta[b]indole-3-carboxylic acid The title compound was prepared in a manner similar to that of Example 1.

EXAMPLE 13

8-Bromo-7-fluoro-5-methyl-3-propyl-1,2,3,4-tetrahydro-cyclopenta[b]indole-3-carboxylic acid The title compound was prepared in a manner similar to that of Example 1.

EXAMPLE 14

3-Allyl-8-cyano-5-fluoro-1,2,3,4-tetrahydro-cyclopenta[b]indole-3-carboxylic acid Compound 3-Allyl-5-bromo-8-fluoro-1,2,3,4-tetrahydro-cyclopenta[b]indole-3-carboxylic acid ethyl ester was made as described above (step 1-3) and was treated with CuCN (40 mg, 0.44 mmol) in 5 mL of 1-methyl-2-pyrrolidione. The reaction mixture was heated at 220° C. in a microwave oven for 20 minutes than cooled to room temperature. 5 mL of water and 5 m L of ethyl acetate was added to the reaction mixture and filtered through celite. The organic layer was washed with brine and collected and concentrated. To this crude solid was added 1 mL of 2.0 M lithium hydroxide aqueous solution and 1 mL of ethanol. The reaction mixture was stirred at room temperature for 2 hours than concentrated. The residue was purified by reverse phase HPLC to give the desired product.

EXAMPLE 15

3-Butyl-8-cyano-5-methyl-1,2,3,4-tetrahydro-cyclopenta[b]indole-3-carboxylic acid The title compound was prepared in a manner similar to that of Example 14.

EXAMPLE 16

3-Butyl-8-cyano-5-fluoro-1,2,3,4-tetrahydro-cyclopenta[b]indole-3-carboxylic acid The title compound was prepared in a manner similar to that of Example 14.

EXAMPLE 17

3-Butyl-8-cyano-7-fluoro-5-methyl-1,2,3,4-tetrahydro-cyclopenta[b]indole-3-carboxylic acid The title compound was prepared in a manner similar to that of Example 14.

EXAMPLE 18

3-Allyl-8-cyano-5-methyl-1,2,3,4-tetrahydro-cyclopenta[b]indole-3-carboxylic acid The title compound was prepared in a manner similar to that of Example 14.

EXAMPLE 19

3-Allyl-8-cyano-7-fluoro-5-methyl-1,2,3,4-tetrahydro-cyclopenta[b]indole-3-carboxylic acid The title compound was prepared in a manner similar to that of Example 14.

EXAMPLE 20

8-Cyano-5-methyl-3-propyl-1,2,3,4-tetrahydro-cyclopenta[b]indole-3-carboxylic acid The title compound was prepared in a manner similar to that of Example 14.

EXAMPLE 21

8-Cyano-5-fluoro-3-propyl-1,2,3,4-tetrahydro-cyclopenta[b]indole-3-carboxylic acid The title compound was prepared in a manner similar to that of Example 14.

EXAMPLE 22

8-Cyano-7-fluoro-5-methyl-3-propyl-1,2,3,4-tetrahydro-cyclopenta[b]indole-3-carboxylic acid The title compound was prepared in a manner similar to that of Example 14.

EXAMPLE 23

5,8-Dichloro-1-ethyl-2,3,4,9-tetrahydro-1H-carbazole-1-carboxylic acid

The title compound was prepared by following a procedure similar to Example 1, for example, where 2-carboethoxy cyclohexanone was used in the place of 2-carbethoxy cyclopentanone in the first step.

EXAMPLE 24

5,8-Dichloro-1-propyl-2,3,4,9-tetrahydro-1H-carbazole-1-carboxylic acid

The title compound was prepared by following a procedure similar to Example 1, for example, where 2-carboethoxy cyclohexanone was used in the place of 2-carbethoxy cyclopentanone in the first step.

EXAMPLE 25

5-Cyano-8-fluoro-1-propyl-2,3,4,9-tetrahydro-1H-carbazole-1-carboxylic acid

The title compound was prepared in a manner similar to that of Example 14.

EXAMPLE 26

5-Cyano-1-cyclobutylmethyl-8-fluoro-2,3,4,9-tetrahydro-1H-carbazole-1-carboxylic acid The title compound was prepared in a manner similar to that of Example 14.

EXAMPLE 27

8-Chloro-1-propyl-5-trifluoromethyl-2,3,4,9-tetrahydro-1H-carbazole-1-carboxylic acid The title compound was prepared following a procedure similar to Example 1, for example, where 2-carboethoxy cyclohexanone was used in the place of 2-carbethoxy cyclopentanone in the first step.

EXAMPLE 28

5-Cyano-8-methyl-1-propyl-2,3,4,9-tetrahydro-1H-carbazole-1-carboxylic acid

The title compound was prepared in a manner similar to that of Example 14.

EXAMPLE 29

(1-Allyl-5,8-difluoro-2,3,4,9-tetrahydro-1H-carbazol-1-yl)-acetic acid

The title compound was synthesized according to the procedure reported in J. Med. Chem. (1988), 31, 2211-17.

EXAMPLE 30

(5,7-Difluoro-1-propyl-2,3,4,9-tetrahydro-1H-carbazol-1-yl)-acetic acid

The title compound was synthesized according to the procedure reported in J. Med. Chem. (1988), 31, 2211-17.

EXAMPLE 31

(1-Allyl-5-cyano-8-fluoro-2,3,4,9-tetrahydro-1H-carbazol-1-yl)-acetic acid

The title compound was synthesized according to the procedure reported in J. Med. Chem. (1988), 31, 2211-17.

EXAMPLE 32

(5-Cyano-8-fluoro-1-propyl-2,3,4,9-tetrahydro-1H-carbazol-1-yl)-acetic acid

The title compound was synthesized according to the procedure reported in J. Med. Chem. (1988), 31, 2211-17.

EXAMPLE 33

(8-Carbamoyl-5-cyano-1-propyl-2,3,4,9-tetrahydro-1H-carbazol-1-yl)-acetic acid

The title compound was synthesized according to the procedure reported in J. Med. Chem. (1988), 31, 2211-17.

EXAMPLE 34

(1-Allyl-5,8-dicyano-2,3,4,9-tetrahydro-1H-carbazol-1-yl)-acetic acid

The title compound was synthesized according to the procedure reported in J. Med. Chem. (1988), 31, 2211-17.

EXAMPLE 35

(5,8-Dicyano-1-propyl-2,3,4,9-tetrahydro-1H-carbazol-1-yl)-acetic acid

The title compound was synthesized according to the procedure reported in J. Med. Chem. (1988), 31, 2211-17.

EXAMPLE 36

(5-Cyano-1-propyl-2,3,4,9-tetrahydro-1H-carbazol-1-yl)-acetic acid

The title compound was synthesized according to the procedure reported in J. Med. Chem. (1988), 31, 2211-17.

The ability of the compounds of formula (I) to inhibit Hepatitis C Polymerase was established by the following experimental procedure.

NS5B from the BK strain (genotype 1b) is expressed in *E coli* as a protein in which the 21 C-terminal amino acids are replaced with a short linker and a hexahistidine tag (GSH-HHHHH). The purified protein is mixed with radioactive nucleotides and allowed to replicate a heteropolymeric RNA substrate, primed by an endogenous short hairpin, resulting in an approximately 760 nt product. The radioactive product is captured on a filter and quantitated after removal of the unincorporated nucleotides.

Reagents:

10 mM uridine 5'-triphosphate (UTP) (Promega # p116B)
10 mM adenine 5'-triphosphate (ATP) (Promega # p113B)
10 mM cytidine 5'-triphosphate (CTP) (Promega # p114B)
10 mM guanine 5'-triphosphate (GTP) (Promega # p115B)
Bovine Serum Albumin (BSA) 10 mg/ml NEB (100× at 10 mg/ml) #007-BSA
RNasein (Promega #N251X) 40 U/μl
A-[$^{33}$P]-GTP (NEN-easytides NEG/606H 3000 Ci/mmol, 370 MBq/ml, 10 mCi/ml)
Falcon polypropylene 96 well plates (Becton Dickinson # 351190)
Millipore Multiscreen assay system-96 well-filtration plate #MADE NOB 50
Optiphase Supermix (Wallac) formulated by Fisher
Millipore Multiscreen liner for use in microbeta 1450-106 casette [(Wallac) Perkin Elmer #1450-433]
1 M (N-[2-hydroxyethyl]piperazine-N'-[2-ethanesulfonic acid]) (HEPES), pH 7.3
Amersham Pharmacia Biotec (US16924-500 ml)
1 M MgCl2 (SIGMA #M1028)
Dithiothreitol (DTT) (solid) (SIGMA # D9779)
RNase free water (GIBCO-BRL #10977-023)
Dimethyl sulfoxide (Aldrich #27685-5)
Basilen Blue (Sigma, B5520)
0.5M ethylenediaminetetraacetic acid (EDTA), pH 8 (GIBCO-BRL #15575-020)
Dibasic sodium phosphate (7-hydrate) (Na2HPO4.7H2O; Baker#3824-07)
Phosphoric acid (Baker, #0262.02)

Further Reagent Preparation:

0.5 M Na Phosphate buffer. Per liter, water is added to 134 grams Na$_2$HPO$_4$7H$_2$O to obtain about 900 ml. The pH is adjusted to 7.0 with phosphoric acid. Water is added to obtain 1 L. Nucleotides are diluted 1:1000 to 10 μM (GTP and CTP) or 1:100 to 100 μM (ATP and UTP) into RNase free water.

Procedure:

(1) Compounds 10 μl at 10 μg/ml in 15% dimethylsulfoxide (DMSO)

When starting from 100 μg/ml compound stock in 1% DMSO, 5 μl 30% DMSO is dispensed per well. Next, 5 μl compound (100 μg/ml) is dispensed per well.

When starting from 50 μg/ml compound stock in 15% DMSO, 10 μl compound is added per well.

(2) Enzyme Mix:

| Stock | Final Conc (in 50 μl assay volume) | Per 20 μl mix (1 reaction) | Per 600 reactions |
|---|---|---|---|
| DEPC H20 | | 17.06 μl | 10236 μl |
| 1 M HEPES, pH 7.5 | 20 mM | 0.5 μl | 300 μl |
| 1 M MgCl2 | 5 mM | 0.25 μl | 150 μl |
| 100 mM DTT | 1 mM | 0.5 μl | 300 μl |
| 100 μM UTP | 0.5 μM | 0.25 μl | 150 μl |
| 100 μM ATP | 1 μM | 0.5 μl | 300 μl |
| 10 μM CTP | 0.08 μM | 0.4 μl | 240 μl |
| 10 μM GTP | 0.025 μM | 0.125 μl | 75 μl |
| BSA, 10 mg/ml | 0.05 mg/ml | 0.25 μl | 150 μl |
| HCV RdRp NS5B d21BK (500 μg/ml or ~7.5 μM) | 24 nM | 0.16 μl | 96 μl |
| Total: | | 20 μl | 12 ml |

20 μl enzyme mix is added into each well of the assay plate. The compound and enzyme are incubated at room temperature for 15 minutes.

(3) Template mix (prepared in advance)

A tube of RNA (5 μg/tube stored in 75% ethanol and 0.3 M sodium acetate) is microcentrifuged for 20 minutes at 4° C. (one tube supplies 1-1.5 plates). Ethanol is removed from the tube by gently inverting the tube. The RNA is vacuum dried and re-suspended in 1 ml of DEPC water in a tightly capped tube. To dissolve RNA, the RNA solution is incubated on ice for ~60 minutes and gently vortexed. It is spun briefly to ensure all RNA solution at the bottom of the tube before opening cap. The RNA solution is then gently transferred into a 5 ml or larger tube. Another 3 ml of DEPC water is added to obtain a total of 4 ml of volume.

The following volumes of reagents are added:

| Stock | Final concentration | Per 20 μl mix (1 reaction) | Per 600 reactions |
|---|---|---|---|
| RNAse-free water | | 2.98 μl | 1788 μl |
| Hepes, 1M | 20 mM | 0.5 μl | 300 μl |
| RNase Inhibitor (40 U/μl) | 0.4 μ/μl | 0.5 μl | 300 μl |
| 33P-GTP 3000 Ci/mmol, 10 μCi/μl (3.3 μM) | 0.025 μM | 0.0125 μl | 7.5 μl |
| POF RNA template | 3 nM | 16 μl | 9600 μl |

20 μl template mix per reaction is added (i.e. 20 ng of pOF per reaction or ~3 nM)

(4) The reaction is incubated at room temperature (22-25° C.) for 2 hours.

(5) The reaction is quenched by adding 50 μl of 170 mM EDTA.

Final concentration of EDTA is 85 mM.

(6) The filters of Millipore multiscreen assay plate is pre-wet by adding 200 μl of 0.5 M sodium phosphate buffer, pH 7.0 into each well. This stands at room temperature for 2-3 minutes.

(7) The multiscreen filter plate is placed onto a Millipore Manifold under vacuum to allow buffer to flow through. After the vacuum is turned off, 80 μl of the reaction product is transferred into each well of the filter plate. This stands for 2-3 minutes prior to turning on the vacuum again to filter the reaction product.

(8) The vacuum is then removed. 200 μl of 0.5 M sodium phosphate buffer is added, pH 7.0, into each well. The vacuum is then turned on.

Step (8) is repeated three more times.

(9) Next the polypropylene bottom is removed, and the filter is spot dried with a paper towel. The filter plate is air-dried on a bench for 1 hour before adding 40 μl Super Mix scintillant. The top of the plate is sealed with a tape and the plate is placed into a Packard carrier or micro-beta carrier.

(10) The plate is counted using a Packard Topcount or micro-beta counter. Count (for example using Program 10) for $^{33}$P in Top count or $^{33}$P program in micro-beta.

The percent inhibition is calculated after background subtraction as a percent reduction of activity relative to the positive control (average value of the plate excluding the negative controls). For the primary screen hits were chosen as showing >75% inhibition.

See, Ferrari et al. 1999. J. Virology 73:1649-1654: "Characterization of soluble Hepatitis C virus RNA-dependent RNA polymerase expressed in *E. coli* and Takamizawa et al 1991" and J. Virology 65:1105-1113: "Structure and characterization of Hepatitis C virus genome isolated from human carriers," both reference are hereby incorporated by reference.

The compounds of the present invention inhibited Hepatitis C polymerase as summarized in Table 1 A and B:

TABLE 1A

| Example | HCV pol BK IC$_{50}$ (μM) |
|---|---|
| 1 | 1.2 |
| 2 | 1.9 |
| 3 | 0.55 |
| 4 | 6.7 |
| 5 | 5.8 |
| 6 | 2.1 |
| 7 | 9.1 |
| 8 | 5.7 |
| 9 | 6.4 |
| 10 | 3.2 |
| 11 | 1.9 |
| 12 | 2.9 |
| 13 | 2 |
| 14 | 14.5 |
| 15 | 4.6 |
| 16 | 5.4 |
| 17 | 1.5 |
| 18 | 11 |
| 19 | 6.3 |
| 20 | 4.7 |
| 21 | 8.1 |
| 22 | 1.8 |
| 23 | 9.7 |
| 24 | 3.2 |
| 25 | 10 |
| 26 | 16 |
| 27 | 5.8 |
| 28 | 15 |
| 29 | 32 |
| 30 | 30.7 |
| 31 | 0.37 |
| 32 | 2 |
| 33 | 5.9 |

TABLE 1A-continued

| Example | HCV pol BK IC$_{50}$ (μM) |
|---|---|
| 34 | 3.4 |
| 35 | 3.4 |
| 36 | 9.5 |

The ability of the compounds of the present invention to inhibit Hepatitis C virus replicon constitutively expressed in a human liver cell line was established by the following experimental procedure:

Clone A cells (licensed from Apath, LLC) are derived from Huh-7 cells (human hepatoma cell line) and constitutively express of the HCV replication proteins with concomitant amplification the HCV replicon (1b) genome. Cells are maintained and passaged in DMEM/10% FCS/1 mg/ml G418 (Geneticin from Gibco #11811-023; other media components as described below in "elisa media"). Care should be taken to maintain cell monolayers at a subconfluent state by 1:3 or 1:4 passages every 3-4 days. The replicon is extremely sensitive to the cellular metabolism/proliferation state and replicon copy number will rapidly decline in confluent monolayers (resting cells). Under ideal conditions each cell has, on average, 1000 copies of the HCV replicon genome.

Regents:

Elisa Media:

Dulbecco's Modified Eagle Media (DMEM) (Gibco #12430-047)

2% Fetal Calf Serum (FCS) (HyClone #SH30070.03)

1× pen/strep (Gibco #15140-122)

1× Non-essential amino acids (NEAA) (Gibco #11140-050)

no G418

Glutaraldehyde (Fisher #02957-4)

TWEEN-20, 10% (Roche #1332465)

TRITON X-100 (Sigma #T-8787)

Superblock in Phosphate Buffered Saline (PBS) (Pierce #37515)

NS5a monoclonal antibody (Virostat #1873)

Goat antimouse-HRP monoclonal antibody (BioRad #172-1011)

3,3',5,5' tetramethylbenzidine (TMB) substrate (Sigma #T-0440)

Compound Dilution/Cell Plating:

Drug Plate Preparation (Mother Plate)

10 μl of compounds (in DMSO) are added to column 3 of the mother plate. 5 μl of DMSO are added to the remaining columns. Mother plates are set aside until ready for serial dilution to be performed.

Control Drugs

Drug and Cell Addition:

The process for each plate involves preparing cell plates (daughter plates) by adding 52 μl of Elisa media to each well. In the Mother plates, 50 μl/well is serially transferred from column 3 through column 12. Next, 8 μl is transferred from the mother plate to daughter plates (all 96 wells). The daughter plates are placed in an incubator until the cells are prepared. The Clone A cells are harvested and plated directly into the daughter plates at 0.7×10$^5$ cells/ml, 100 μl/well. Finally, all plates are incubated at 37° C. in 5% CO$_2$ for 3 days.

Elisa Assay:

The media is removed from 96-well plates (cells should be ca 80% confluent) by flicking into sink. Next, 130 μl/well 1×PBS+0.05% glutaraldehyde is added, and this is incubated at 37° C. for 1 hour. Again, the media is removed by flicking into sink. The plates are washed 3× with 300 μl/well PBS, shaken 5 min for each wash, and the media is removed by flicking into sink. Then 130 μl/well PBS+0.05% TWEEN-20+0.1% TRITON X-100 is added and the plates are incubated at 37° C. for 10 minutes. The media is removed by flicking into sink and 300 μl/well Superblock in PBS is added. It is again incubated at 37° C. for 1 hour. The media is removed by flicking into sink.

It is then washed 3× with 300 μl/well PBS, shaken 5 minutes for each wash, and the media is removed by flicking into sink. During the last wash, a 1:100 dilution of NS5a Monoclonal-antibody (Mab) in Superblock+0.02% TWEEN-20 is made. After the last wash, 50 μl/well diluted Mab is added. This is incubated at 37° C. for 1 hour, and the media is removed by flicking into sink. Next, it is washed 3× with 300 μl/well PBS+0.02% TWEEN-20, shaken 5 minutes each wash and removed by flicking into sink. During last wash, a 1:500 dilution of goat antimouse-HRP Mab in Superblock+0.02% TWEEN-20 is made. After the last wash, 50 μl/well diluted Mab is added. It is incubated at 37° C. for 1 hour, and removed by flicking into sink. Next, it is washed 5× with 300 μl/well PBS+0.02% TWEEN-20, shaken 5 minutes with each wash and removed by flicking into sink. Then it is washed 3× with 300 μl/well PBS, shaken 5 minutes with each wash, and removed by flicking into sink. After the last wash, 130 μl/well room temperature TMB substrate is added and it is incubated until a blue color develops. Then 130 μl/well 1N HCl is added to stop the reaction (e.g., when the color turns from blue to yellow). The plates are read with optical density (O.D.) 450 filter.

ANALYSIS OF RESULTS: $IC_{50}$ (μM); $IC_{50}$ (μg/ml); % Inhibition

REFERENCE COMPOUNDS: Interferon-$a_2$; 4-30 U/ml IC50

TABLE 2

Pyranoindole derivatives

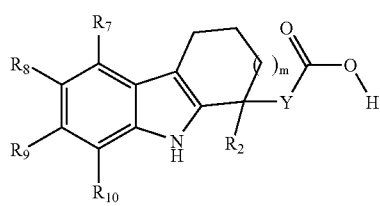

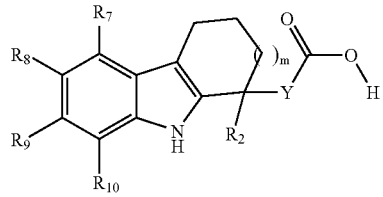

| Example | R2 | R7 | R8 | R10 | m | Y | LC @ 254 minutes | MS (M − H) |
|---|---|---|---|---|---|---|---|---|
| 1 | Allyl | Cl | H | Cl | 0 | — | 3.1 | 309 |
| 2 | n-butyl | Cl | H | Cl | 0 | — | 3.4 | 326, 324 |
| 3 | n-propyl | Cl | H | Cl | 0 | — | 3.27 | 310, 312 |
| 4 | n-butyl | Br | H | $CH_3$ | 0 | — | 3.4 | 348, 350 |
| 5 | n-butyl | Br | H | F | 0 | — | 3.4 | 352, 354 |
| 6 | n-butyl | Br | F | $CH_3$ | 0 | — | 3.3 | 366, 368 |
| 7 | n-butyl | H | F | $CH_3$ | 0 | — | 3.2 | 288 |
| 8 | Allyl | Br | H | $CH_3$ | 0 | — | 3.1 | 332, 334 |
| 9 | Allyl | Br | H | F | 0 | — | 3.0 | 336, 338 |
| 10 | Allyl | Br | F | $CH_3$ | 0 | — | 3.1 | 350, 352 |
| 11 | n-propyl | Br | H | $CH_3$ | 0 | — | 3.2 | 338, 336 |
| 12 | n-propyl | Br | H | F | 0 | — | 3.2 | 340, 338 |
| 13 | n-propyl | Br | F | $CH_3$ | 0 | — | 3.1 | 352, 354 |
| 14 | Allyl | CN | H | F | 0 | — | 2.4 | 283 |
| 15 | n-butyl | CN | H | $CH_3$ | 0 | — | 2.8 | 295 |
| 16 | n-butyl | CN | H | F | 0 | — | 2.7 | 299 |
| 17 | n-butyl | CN | F | $CH_3$ | 0 | — | 2.9 | 313 |
| 18 | Allyl | CN | H | $CH_3$ | 0 | — | 2.5 | 279 |
| 19 | Allyl | CN | F | $CH_3$ | 0 | — | 2.6 | 297 |
| 20 | n-propyl | CN | H | $CH_3$ | 0 | — | 2.6 | 281 |
| 21 | n-propyl | CN | H | F | 0 | — | 2.6 | 285 |
| 22 | n-propyl | CN | F | $CH_3$ | 0 | — | 2.7 | 299 |
| 23 | Ethyl | Cl | H | Cl | 1 | — | 3.27 | 311 |
| 24 | n-propyl | Cl | H | Cl | 1 | — | 2.98 | 325 |
| 25 | n-propyl | CN | H | F | 1 | — | 2.78 | 299 |
| 26 | $CH_2$-c-butyl | CN | H | F | 1 | — | 3.06 | 325 |
| 27 | n-propyl | $CF_3$ | H | Cl | 1 | — | 3.50 | 358 |
| 28 | n-propyl | CN | H | $CH_3$ | 1 | — | 2.89 | 295 |
| 29 | Allyl | F | H | F | 1 | $CH_2$ | — | — |
| 30 | n-propyl | H | F | F | 1 | $CH_2$ | — | — |
| 31 | Allyl | CN | H | F | 1 | $CH_2$ | — | — |
| 32 | n-propyl | CN | H | F | 1 | $CH_2$ | — | — |
| 33 | n-propyl | $CONH_2$ | H | F | 1 | $CH_2$ | — | — |
| 34 | Allyl | CN | H | CN | 1 | $CH_2$ | — | — |
| 35 | n-propyl | CN | H | CN | 1 | $CH_2$ | — | — |
| 36 | n-propyl | CN | H | H | 1 | $CH_2$ | — | — |

We claim:

1. A compound of formula (I):

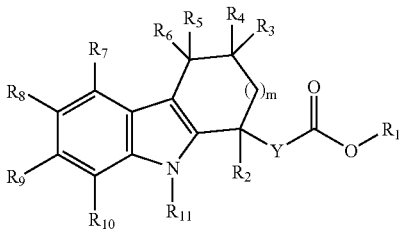

wherein:

m=0;

$R_1$ is a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, or an alkynyl of 2 to 7 carbon atoms;

$R_2$ is a straight chain alkyl of 2 to 12 carbon atoms, a branched alkyl of 3 to 12 carbon atoms, a cycloalkyl of 3 to 12 carbon atoms, a cycloalkyl-alkyl of 4 to 24 carbon atoms, an alkenyl of 2 to 7 carbon atoms, or an alkynyl of 2 to 7 carbon atoms;

$R_3$-$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, or an alkynyl of 2 to 7 carbon atoms;

$R_7$-$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, an alkynyl of 2 to 7 carbon atoms, an alkoxy of 1 to 8 carbon atoms, an alkylthio of 1 to 8 carbon atoms, trifluoromethoxy, trifluoroethoxy, trifluoromethylthio, trifluoroethylthio, an acyl of 1 to 7 carbon atoms, COOH, COO-alkyl, $CONR_{12}R_{13}$, F, Cl, Br, I, CN, $CF_3$, $NO_2$, an alkylsulfinyl of 1 to 8 carbon atoms, or an alkylsulfonyl of 1 to 6 carbon atoms;

$R_{11}$ is H, a straight chain alkyl of 1 to 6 carbon atoms, a branched alkyl of 3 to 10 carbon atoms, a cycloalkyl of 3 to 10 carbon atoms, or an alkenyl of 2 to 7 carbon atoms;

$R_{12}$-$R_{13}$ are independently H, a straight chain alkyl of 1 to 8 carbon atoms, a branched alkyl of 3 to 12 carbon atoms, or a cycloalkyl of 3 to 12 carbon atoms; and Y is a bond, or a pharmaceutically acceptable salt thereof.

2. The compound of claim 1, wherein $R_3$, $R_4$, $R_5$ and $R_6$ are H.

3. The compound of claim 2, wherein $R_{11}$ is H.

4. The compound of claim 3, wherein $R_7$ and $R_{10}$ are independently selected from H, Cl, Br, F, $CF_3$, CN, $CONH_2$ and $CH_3$.

5. The compound of claim 3, wherein $R_8$ is H or F.

6. The compound of claim 3, wherein $R_2$ is allyl, n-butyl, n-propyl, ethyl or $CH_2$—C-butyl.

7. The compound of claim 1, wherein $R_7$ and $R_{10}$ are independently selected from H, Cl, Br, F, $CF_3$, CN, $CONH_2$ and $CH_3$; $R_8$ is H or F; and $R_2$ is allyl, n-butyl, n-propyl, ethyl or $CH_2$—C-butyl.

8. The compound of claim 7, wherein $R_3$, $R_4$, $R_5$, $R_6$ and $R_{11}$ are H.

9. The compound of claim 1, selected from the group consisting of:

3-Allyl-5,8-dichloro-1,2,3,4-tetrahydro-cyclopenta[b]indole-3-carboxylic acid ethyl ester;
3-Butyl-5,8-dichloro-1,2,3,4-tetrahydro-cyclopenta[b]indole-3-carboxylic acid ethyl ester;
5,8-Dichloro-3-propyl-1,2,3,4-tetrahydro-cyclopenta[b]indole-3-carboxylic acid ethyl ester;
8-Bromo-3-butyl-5-methyl-1,2,3,4-tetrahydro-cyclopenta[b]indole-3-carboxylic acid ethyl ester;
8-Bromo-3-butyl-5-fluoro-1,2,3,4-tetrahydro-cyclopenta[b]indole-3-carboxylic acid ethyl ester;
8-Bromo-3-butyl-7-fluoro-5-methyl-1,2,3,4-tetrahydro-cyclopenta[b]indole-3-carboxylic acid ethyl ester;
3-Butyl-7-fluoro-5-methyl-1,2,3,4-tetrahydro-cyclopenta[b]indole-3-carboxylic acid ethyl ester;
3-Allyl-8-bromo-5-methyl-1,2,3,4-tetrahydro-cyclopenta[b]indole-3-carboxylic acid ethyl ester;
3-Allyl-8-bromo-5-fluoro-1,2,3,4-tetrahydro-cyclopenta[b]indole-3-carboxylic acid ethyl ester;
3-Allyl-8-bromo-7-fluoro-5-methyl-1,2,3,4-tetrahydro-cyclopenta[b]indole-3-carboxylic acid ethyl ester;
8-Bromo-5-methyl-3-propyl-1,2,3,4-tetrahydro-cyclopenta[b]indole-3-carboxylicacid carboxylic acid ethyl ester;
8-Bromo-5-fluoro-3-propyl-1,2,3,4-tetrahydro-cyclopenta[b]indole-3-carboxylic acid ethyl ester;
8-Bromo-7-fluoro-5-methyl-3-propyl-1,2,3,4-tetrahydro-cyclopenta[b]indole-3-carboxylic acid ethyl ester;
3-Allyl-8-cyano-5-fluoro-1,2,3,4-tetrahydro-cyclopenta[b]indole-3-carboxylic acid ethyl ester;
3-Butyl-8-cyano-5-methyl-1,2,3,4-tetrahydro-cyclopenta[b]indole-3-carboxylic acid ethyl ester;
3-Butyl-8-cyano-5-fluoro-1,2,3,4-tetrahydro-cyclopenta[b]indole-3-carboxylic acid ethyl ester;
3-Butyl-8-cyano-7-fluoro-5-methyl-1,2,3,4-tetrahydro-cyclopenta[b]indole-3-carboxylic acid ethyl ester;
3-Allyl-8-cyano-5-methyl-1,2,3,4-tetrahydro-cyclopenta[b]indole-3-carboxylic acid ethyl ester;
3-Allyl-8-cyano-7-fluoro-5-methyl-1,2,3,4-tetrahydro-cyclopenta[b]indole-3-carboxylic acid ethyl ester;
8-Cyano-5-methyl-3-propyl-1,2,3,4-tetrahydro-cyclopenta[b]indole-3-carboxylic acid ethyl ester;
8-Cyano-5-fluoro-3-propyl-1,2,3,4-tetrahydro-cyclopenta[b]indole-3-carboxylic acid ethyl ester; and
8-Cyano-7-fluoro-5-methyl-3-propyl-1,2,3,4-tetrahydro-cyclopenta[b]indole-3-carboxylic acid ethyl ester.

10. A pharmaceutical composition used for the treatment of HCV comprising a compound of formula (I):

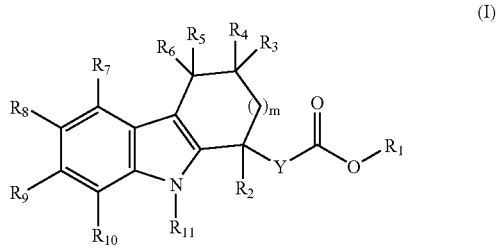

wherein:

m=0;

$R_1$ is a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, or an alkynyl of 2 to 7 carbon atoms;

$R_2$ is a straight chain alkyl of 2 to 12 carbon atoms, a branched alkyl of 3 to 12 carbon atoms, a cycloalkyl of 3 to 12 carbon atoms, a cycloalkyl-alkyl of 4 to 24 carbon atoms, an alkenyl of 2 to 7 carbon atoms, or an alkynyl of 2 to 7 carbon atoms;

$R_3$-$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, or an alkynyl of 2 to 7 carbon atoms;

$R_7$-$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, an alkynyl of 2 to 7 carbon atoms, an alkoxy of 1 to 8 carbon atoms, an alkylthio of 1 to 8 carbon atoms, trifluoromethoxy, trifluoroethoxy, trifluoromethylthio, trifluoroethylthio, an acyl of 1 to 7 carbon atoms, COOH, COO-alkyl, $CONR_{12}R_{13}$, F, Cl, Br, I, CN, $CF_3$, $NO_2$, an alkylsulfinyl of 1 to 8 carbon atoms, or an alkylsulfonyl of 1 to 6 carbon atoms;

$R_{11}$ is H, a straight chain alkyl of 1 to 6 carbon atoms, a branched alkyl of 3 to 10 carbon atoms, a cycloalkyl of 3 to 10 carbon atoms, or an alkenyl of 2 to 7 carbon atoms;

$R_{12}$-$R_{13}$ are independently H, a straight chain alkyl of 1 to 8 carbon atoms, a branched alkyl of 3 to 12 carbon atoms, or a cycloalkyl of 3 to 12 carbon atoms; and Y is a bond,
or a pharmaceutically acceptable salt thereof; and
a pharmaceutically acceptable carrier.

11. The pharmaceutical composition of claim 10, wherein $R_3$, $R_4$, $R_5$ and $R_6$ are H.

12. The pharmaceutical composition of claim 11, wherein $R_{11}$ is H.

13. The pharmaceutical composition of claim 12, wherein $R_7$ and $R_{10}$ are independently selected from H, Cl, Br, F, $CF_3$, CN, $CONH_2$ and $CH_3$.

14. The pharmaceutical composition of claim 12, wherein $R_8$ is H or F.

15. The pharmaceutical composition of claim 12, wherein $R_2$ is allyl, n-butyl, n-propyl, ethyl or $CH_2$—C-butyl.

16. The pharmaceutical composition of claim 10, wherein $R_7$ and $R_{10}$ are independently selected from H, Cl, Br, F, $CF_3$, CN, $CONH_2$ and $CH_3$; $R_8$ is H or F; and $R_2$ is allyl, n-butyl, n-propyl, ethyl or $CH_2$—C-butyl.

17. The pharmaceutical composition of claim 16, wherein $R_3$, $R_4$, $R_5$, $R_6$ and $R_{11}$ are H.

18. The pharmaceutical composition of claim 10, wherein the compound of formula (I) is selected from the group consisting of:
  3-Allyl-5,8-dichloro-1,2,3,4-tetrahydro-cyclopenta[b]indole-3-carboxylic acid ethyl ester;
  3-Butyl-5,8-dichloro-1,2,3,4-tetrahydro-cyclopenta[b]indole-3-carboxylic acid ethyl ester;
  5,8-Dichloro-3-propyl-1,2,3,4-tetrahydro-cyclopenta[b]indole-3-carboxylic acid ethyl ester;
  8-Bromo-3-butyl-5-methyl-1,2,3,4-tetrahydro-cyclopenta[b]indole-3-carboxylic acid ethyl ester;
  8-Bromo-3-butyl-5-fluoro-1,2,3,4-tetrahydro-cyclopenta[b]indole-3-carboxylic acid ethyl ester;
  8-Bromo-3-butyl-7-fluoro-5-methyl-1,2,3,4-tetrahydro-cyclopenta[b]indole-3-carboxylic acid ethyl ester;
  3-Butyl-7-fluoro-5-methyl-1,2,3,4-tetrahydro-cyclopenta[b]indole-3-carboxylic acid ethyl ester;
  3-Allyl-8-bromo-5-methyl-1,2,3,4-tetrahydro-cyclopenta[b]indole-3-carboxylic acid ethyl ester;
  3-Allyl-8-bromo-5-fluoro-1,2,3,4-tetrahydro-cyclopenta[b]indole-3-carboxylic acid ethyl ester;
  3-Allyl-8-bromo-7-fluoro-5-methyl-1,2,3,4-tetrahydro-cyclopenta[b]indole-3-carboxylic acid ethyl ester;
  8-Bromo-5-methyl-3-propyl-1,2,3,4-tetrahydro-cyclopenta[b]indole-3-carboxylicacid carboxylic acid ethyl ester;
  8-Bromo-5-fluoro-3-propyl-1,2,3,4-tetrahydro-cyclopenta[b]indole-3-carboxylic acid ethyl ester;
  8-Bromo-7-fluoro-5-methyl-3-propyl-1,2,3,4-tetrahydro-cyclopenta[b]indole-3-carboxylic acid ethyl ester;
  3-Allyl-8-cyano-5-fluoro-1,2,3,4-tetrahydro-cyclopenta[b]indole-3-carboxylic acid ethyl ester;
  3-Butyl-8-cyano-5-methyl-1,2,3,4-tetrahydro-cyclopenta[b]indole-3-carboxylic acid ethyl ester;
  3-Butyl-8-cyano-5-fluoro-1,2,3,4-tetrahydro-cyclopenta[b]indole-3-carboxylic acid ethyl ester;
  3-Butyl-8-cyano-7-fluoro-5-methyl-1,2,3,4-tetrahydro-cyclopenta[b]indole-3-carboxylic acid ethyl ester;
  3-Allyl-8-cyano-5-methyl-1,2,3,4-tetrahydro-cyclopenta[b]indole-3-carboxylic acid ethyl ester;
  3-Allyl-8-cyano-7-fluoro-5-methyl-1,2,3,4-tetrahydro-cyclopenta[b]indole-3-carboxylic acid ethyl ester;
  8-Cyano-5-methyl-3-propyl-1,2,3,4-tetrahydro-cyclopenta[b]indole-3-carboxylic acid ethyl ester;
  8-Cyano-5-fluoro-3-propyl-1,2,3,4-tetrahydro-cyclopenta[b]indole-3-carboxylic acid ethyl ester and
  8-Cyano-7-fluoro-5-methyl-3-propyl-1,2,3,4-tetrahydro-cyclopenta[b]indole-3-carboxylic acid ethyl ester.

19. A method for treating hepatitis C infection in a mammal comprising administering to said mammal an amount effective to treat the infection of at least one compound of formula I,

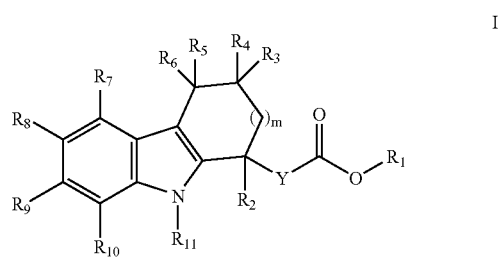

wherein:
m=0;
$R_1$ is a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, or an alkynyl of 2 to 7 carbon atoms;
$R_2$ is a straight chain alkyl of 2 to 12 carbon atoms, a branched alkyl of 3 to 12 carbon atoms, a cycloalkyl of 3 to 12 carbon atoms, a cycloalkyl-alkyl of 4 to 24 carbon atoms, an alkenyl of 2 to 7 carbon atoms, or an alkynyl of 2 to 7 carbon atoms;
$R_3$-$R_6$ are independently H, a straight chain alkyl of 1 to 8 carbon atoms, a branched alkyl of 3 to 12 carbon atoms, a cycloalkyl of 3 to 12 carbon atoms, an alkenyl of 2 to 7 carbon atoms, or an alkynyl of 2 to 7 carbon atoms;
$R_7$-$R_{10}$ are independently H, a straight chain alkyl of 1 to 8 carbon atoms, a branched alkyl of 3 to 12 carbons atoms, a cycloalkyl of 3 to 12 carbon atoms, an alkenyl of 2 to 7 carbon atoms, an alkynyl of 2 to 7 carbon atoms, an alkoxy of 1 to 8 carbon atoms, an alkylthio of 1 to 8 carbon atoms, trifluoromethoxy, trifluoroethoxy, trifluoromethylthio, trifluoroethylthio, an acyl of 1 to 7 carbon atoms, COOH, COO-alkyl, $CONR_{12}R_{13}$, F, Cl, Br, I, CN, $CF_3$, $NO_2$, an alkylsulfinyl of 1 to 8 carbon atoms, or an alkylsulfonyl of 1 to 6 carbon atoms;
$R_{11}$ is H, a straight chain alkyl of 1 to 6 carbon atoms, a branched alkyl of 3 to 10 carbon atoms, a cycloalkyl of 3 to 10 carbon atoms, or an alkenyl of 2 to 7 carbon atoms;
$R_{12}$-$R_{13}$ are independently H, a straight chain alkyl of 1 to 8 carbon atoms, a branched alkyl of 3 to 12 carbon atoms, or a cycloalkyl of 3 to 12 carbon atoms; and
Y is a bond,
or a pharmaceutically acceptable salt thereof; and
a pharmaceutically acceptable carrier.

20. The method of claim 19, wherein the mammal is a human.

21. The method of claim 19, wherein $R_3$, $R_4$, $R_5$ and $R_6$ are H.

22. The method of claim 21, wherein $R_{11}$ is H.

23. The method of claim 22, wherein $R_7$ and $R_{10}$ are independently selected from H, Cl, Br, F, $CF_3$, CN, $CONH_2$ and $CH_3$.

24. The method of claim 22, wherein $R_8$ is H or F.

25. The method of claim 22, wherein $R_2$ is allyl, n-butyl, n-propyl, ethyl or $CH_2$—C-butyl.

26. The method of claim 19, wherein $R_7$ and $R_{10}$ are independently selected from H, Cl, Br, F, $CF_3$, CN, $CONH_2$ and $CH_3$; $R_8$ is H or F; and $R_2$ is allyl, n-butyl, n-propyl, ethyl or $CH_2$—C-butyl.

27. The method of claim 26, wherein $R_3$, $R_4$, $R_5$, $R_6$ and $R_{11}$ are H.

28. The method of claim 19, wherein the compound of formula (I) is selected from the group consisting of:
- 3-Allyl-5,8-dichloro-1,2,3,4-tetrahydro-cyclopenta[b]indole-3-carboxylic acid ethyl ester;
- 3-Butyl-5,8-dichloro-1,2,3,4-tetrahydro-cyclopenta[b]indole-3-carboxylic acid ethyl ester;
- 5,8-Dichloro-3-propyl-1,2,3,4-tetrahydro-cyclopenta[b]indole-3-carboxylic acid ethyl ester;
- 8-Bromo-3-butyl-5-methyl-1,2,3,4-tetrahydro-cyclopenta[b]indole-3-carboxylic acid ethyl ester;
- 8-Bromo-3-butyl-5-fluoro-1,2,3,4-tetrahydro-cyclopenta[b]indole-3-carboxylic acid ethyl ester;
- 8-Bromo-3-butyl-7-fluoro-5-methyl-1,2,3,4-tetrahydro-cyclopenta[b]indole-3-carboxylic acid ethyl ester;
- 3-Butyl-7-fluoro-5-methyl-1,2,3,4-tetrahydro-cyclopenta[b]indole-3-carboxylic acid ethyl ester;
- 3-Allyl-8-bromo-5-methyl-1,2,3,4-tetrahydro-cyclopenta[b]indole-3-carboxylic acid ethyl ester;
- 3-Allyl-8-bromo-5-fluoro-1,2,3,4-tetrahydro-cyclopenta[b]indole-3-carboxylic acid ethyl ester;
- 3-Allyl-8-bromo-7-fluoro-5-methyl-1,2,3,4-tetrahydro-cyclopenta[b]indole-3-carboxylic acid ethyl ester;
- 8-Bromo-5-methyl-3-propyl-1,2,3,4-tetrahydro-cyclopenta[b]indole-3-carboxylicacid carboxylic acid ethyl ester;
- 8-Bromo-5-fluoro-3-propyl-1,2,3,4-tetrahydro-cyclopenta[b]indole-3-carboxylic acid ethyl ester;
- 8-Bromo-7-fluoro-5-methyl-3-propyl-1,2,3,4-tetrahydro-cyclopenta[b]indole-3-carboxylic acid ethyl ester;
- 3-Allyl-8-cyano-5-fluoro-1,2,3,4-tetrahydro-cyclopenta[b]indole-3-carboxylic acid ethyl ester;
- 3-Butyl-8-cyano-5-methyl-1,2,3,4-tetrahydro-cyclopenta[b]indole-3-carboxylic acid ethyl ester;
- 3-Butyl-8-cyano-5-fluoro-1,2,3,4-tetrahydro-cyclopenta[b]indole-3-carboxylic acid ethyl ester;
- 3-Butyl-8-cyano-7-fluoro-5-methyl-1,2,3,4-tetrahydro-cyclopenta[b]indole-3-carboxylic acid ethyl ester;
- 3-Allyl-8-cyano-5-methyl-1,2,3,4-tetrahydro-cyclopenta[b]indole-3-carboxylic acid ethyl ester;
- 3-Allyl-8-cyano-7-fluoro-5-methyl-1,2,3,4-tetrahydro-cyclopenta[b]indole-3-carboxylic acid ethyl ester;
- 8-Cyano-5-methyl-3-propyl-1,2,3,4-tetrahydro-cyclopenta[b]indole-3-carboxylic acid ethyl ester;
- 8-Cyano-5-fluoro-3-propyl-1,2,3,4-tetrahydro-cyclopenta[b]indole-3-carboxylic acid ethyl ester; and
- 8-Cyano-7-fluoro-5-methyl-3-propyl-1,2,3,4-tetrahydro-cyclopenta[b]indole-3-carboxylic acid ethyl ester.

29. The compound of claim 1, wherein the compound of formula (I) is 5,8-dichloro-3-propyl-1,2,3,4-tetrahydro-cyclopenta[b]indole-3-carboxylic acid ethyl ester.

30. The pharmaceutical composition of claim 10, wherein the compound of formula (I) is 5,8-dichloro-3-propyl-1,2,3,4-tetrahydro-cyclopenta[b]indole-3-carboxylic acid ethyl ester.

31. The method of claim 19, wherein the compound of formula (I) is 5,8-dichloro-3-propyl-1,2,3,4-tetrahydro-cyclopenta[b]indole-3-carboxylic acid ethyl ester.

* * * * *